Figure 1:
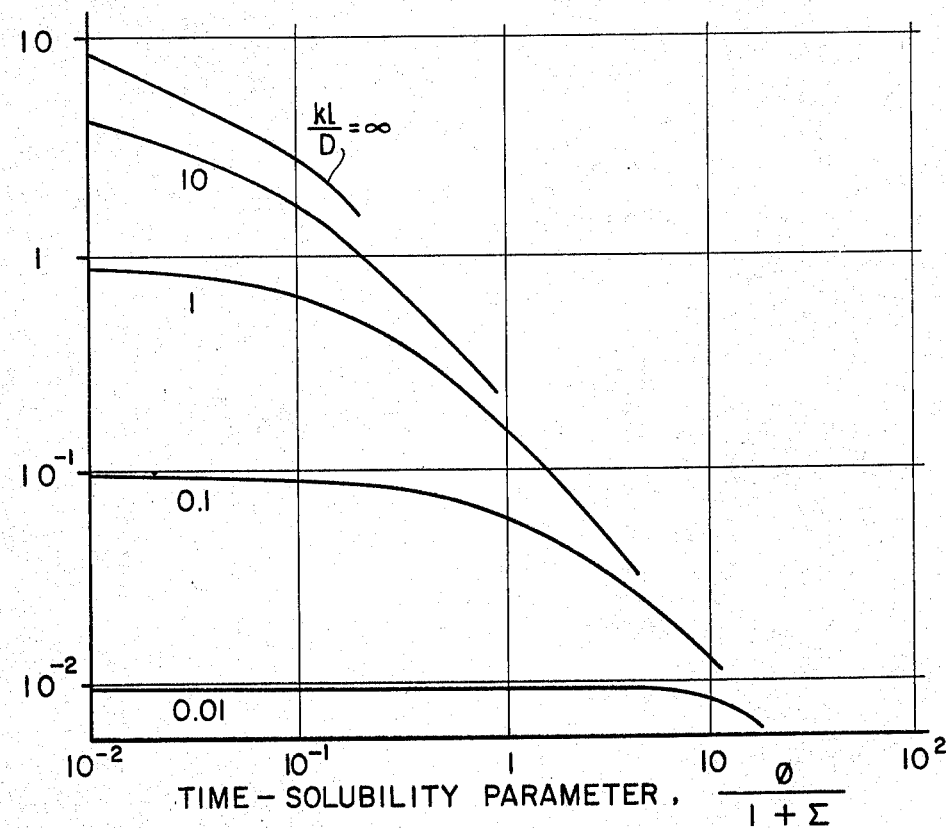

United States Patent
Sadek

[11] 3,976,071
[45] Aug. 24, 1976

[54] METHODS OF IMPROVING CONTROL OF RELEASE RATES AND PRODUCTS USEFUL IN SAME

[75] Inventor: Safik E. Sadek, Wayland, Mass.

[73] Assignee: Dynatech Corporation, Burlington, Mass.

[22] Filed: Jan. 7, 1974

[21] Appl. No.: 431,493

[52] U.S. Cl.................................. 128/260; 424/19; 424/22; 128/335.5
[51] Int. Cl.². .................. A61K 27/12; A61M 31/00
[58] Field of Search................ 128/260, 335.5, 272; 424/19 X, 24, 16, 22, 78; 260/78.3 X

[56] References Cited
UNITED STATES PATENTS

| | | | |
|---|---|---|---|
| 3,225,766 | 12/1965 | Baptist et al......................... | 128/260 |
| 3,435,008 | 3/1969 | Schmitt et al...................... | 260/78.3 |
| 3,545,439 | 12/1970 | Duncan.............................. | 128/260 |
| 3,630,200 | 12/1971 | Higuchi.............................. | 128/260 |
| 3,641,237 | 2/1972 | Gould et al. ......................... | 424/16 |
| 3,773,919 | 11/1973 | Boswell et al........................ | 424/19 |
| 3,810,458 | 5/1974 | Semp .............................. | 128/260 X |
| 3,811,444 | 5/1974 | Heller................................ | 128/260 |
| 3,887,699 | 6/1975 | Yolles................................. | 424/19 |

FOREIGN PATENTS OR APPLICATIONS 2,218,200  10/1972  Germany........................... 128/260

Primary Examiner—Aldrich F. Medbery
Attorney, Agent, or Firm—Cesari and McKenna

[57] ABSTRACT

Improved processes for obtaining the sustained release of pharmaceuticals from polymer matrices comprising the utilization of such steps as will allow the formation of solid solutions between pharmaceutical and its matrix or, conversely and in a proper case, substantially avoiding formation of any solid solution between the matrix and pharmaceutical. The advantage of such processes is the greater predictability of qualitative and quantitative nature of release rates of products formed therewith.

22 Claims, 2 Drawing Figures

METHODS OF IMPROVING CONTROL OF RELEASE RATES AND PRODUCTS USEFUL IN SAME

BACKGROUND OF THE DISCLOSURE

In recent years much research work has been done in development of systems for use in release of active chemicals, over a period of time, into host systems. Such host systems include the human body, soil systems, aquatic bodies; the active ingredients for each such host could be, e.g., antibiotics, insecticides, or herbicides.

Much of the work has been directed towards the development of polymer matrices that will decompose harmlessly in the host system. A series of patents issued to Schmitt et al (e.g. U.S. Pat. No. 3,736,646 which lists a number of other such patents) describes a considerable amount of work related to polymers of polylactic and polyglycolic acid in various applications. Usually the polymer is used as an absorbable suture or bone pin - but use of such polymers as a matrix for pharmaceutical products such as steroids is also disclosed generally. In addition, lipid and protein vehicles have been used as release-moderating matrices relying on enzymatically-accentuated release (U.S. Pat. No. 3,493,652). U.S. Pat. No. 3,279,996 discloses diffusion of drug through polymer walls and describes the rate of release of drug molecules from the implant as a function of the degree of solubility of the drug in silicone rubber.

In general the prior art has been directed toward (1) obtaining polymers which are decomposable within the host system into physiologically-tolerable products which can be disposed of by the metabolism of the host system (2) to attempting achieve a predictable release rate from such products during their effective medication period. Usually the investigators have modified the release rate by (1) using concentration gradients of the active agent in the matrix, (2) selecting shape and size of the articles or (3) limiting diffusion rates by use of semipermeable barrier layers. Scuh investigators have largely accepted the compositions which are most readily obtained by combining matrix and active ingredient.

Applicants, as will be described below, have not followed this procedure but have discovered that significant advances in predictability and control of release rates can be made by careful control of the interaction between matrix and the active agent.

Definitions

The term "matrix" and "active agent" as used herein refer to materials which have little or no chemical reactivity one with the other; i.e., they do not substantially interact to form distinct chemical compounds.

Moreover, the term "matrix" used herein relates to a polymer system wherein the matrix is sufficiently resistant to chemical attack by the host system, e.g. a human body, that it remains substantially intact during the entire release period. Particular emphasis is placed on the poly(glycolic acid) type matrices, especially poly(lactic acid) matrices.

SUMMARY OF THE INVENTION

It is a principal object of the instant invention to provide processes, and novel products produced by such processes, which can be utilized to achieve more predictable release rates from active agents carried in matrices which decompose in situ.

It is a particular object of the invention to provide such processes and products which allow the controlled release of medicine from matrices which decompose into physiologically-tolerable decomposition products after the substantial completion of the medication period.

Another object of the invention is to provide products which are solid solutions of the active agent in the matrix.

A further object of the invention is to provide processes and products wherein a natural tendency to form a solid solution has been suppressed by the mode of manufacture.

Other objects of the invention will be obvious to those skilled in the art on reading this disclosure.

The instant invention is a consequence of applicant's recognition of the existence of substantially different release characteristics between implants (1) comprising an active agent which is discretely dispersed as a solid in a matrix and (2) comprising an active agent which is entirely dissolved in its polymeric matrix.

In effect, applicant, by avoiding any substantial quantity of non-dissolved active agent, has been able to formulate novel solid solutions having particular release rate characteristics. Moreover, by taking positive steps to avoid solid solutions where they would otherwise occur, applicant has been able to achieve predictable release rate characteristics which are not affected by the potential for solubility of the active agent in the matrix.

In general applicant has determined that random combinations of polymer and matrix which are partly solid solutions and partly 2-phase solid mixtures are more difficult to utilize in controlled release work. Consequently, he has developed novel processes and products utilizing this fact.

The general principles developed by applicant can be utilized in implants in various host media: soil, the atmosphere, physiological hosts such as the human body. The most beneficial advances are in such physiological hosts and, in particular, in the dispensing of complex organic chemicals like steroids, say for use in contraceptive applications, in the body over a period of time.

The formulator of a sustained release source of a medicament desires to deliver to the individual treated a specific drug. A set of chemical and physical characteristics is imposed by the drug to be used. Of particular importance is the solubility of the drug in the tissue fluids. The formulator also knows that a given drug should be administered at a given rate and for a specific period. Experience may dictate a maximum period of drug administration. Thus the formulator usually has established for him three important factors: drug solubility, rate of release, and duration of release.

Two other qualities of importance to the delivery of drug from an implanted source have also been identified. These are (1) the diffusivity of the drug in the source matrix and (2) the mass transfer coefficient in the tissues surrounding the sustained release source. These qualities have been found to be of outstanding importance in determining the rate and duration of release from a source under circumstances in which release is predominantly by permeation of the source and diffusional extraction from the source rather than by release upon hydrolysis of the enclosing polymer.

The diffusivity of the drug commonly expressed as D in units of cm$^2$/day, can be the same in the tissue fluids surrounding the source and within the source itself. The mass transfer coefficient of the drug in the vicinity of the source is determined by the vigor of tissue fluid circulation nearby. The mass transfer coefficient will be low in regions where tissue fluids move slowly, such as fatty tissues, e.g. the ear lobe. In more richly vascularized regions the mass transfer coefficient will be relatively higher. These differences enable selection of implant site as one means of regulating dose rate and duration of drug delivery.

With this understanding of drug release by diffusion within tissue fluids which are permeating a sustained release source, it has been discovered that one may select matrix polymer, implant size, and shape by the following procedure: One can estimate the mass transfer coefficient, $k$ (in cm/day) at the desired location of implantation. We may then calculate a dimensionless quantity $kL/D$, where L is the controlling dimension of a proposed implant particle (e.g. as the half-thickness of a flat platelet, or the radius of a spheroid or a cylindrical implant) and D is the diffusivity of the drug through the implant matrix.

When this is done with solid solutions, it has been determined that one may proceed to generalized charts, prepared in advance showing $kL/D$ as one parameter, and relating the fraction of the drug released and the release rate of the drug (expressed in terms of another parameter, $RL/DC$) to the elapsed time of release. FIG. 1 is such a chart relating to solid solutions whereon the elapsed time of release can be expressed as:

$$\frac{\phi}{1+\epsilon}$$

where
R = drug release rate in mass of drug per unit time per unit area of implant surface
C = initial saturation concentration of drug in tissue fluid
$\phi = D\theta/L^2$
$\theta$ = time
$\epsilon$ = a constant whose value depends on density of the polymer, concentration of drug therein, and density of tissue fluid, chemical structures of drug and matrix.

From such charts it is possible to define the duration of the drug release period and the loading of the drug required to provide the desired average release rate for an acceptable implant area.

The dimensionless time just cited is applicable to combinations of drug and matrix for which a solid solution of drug in the polymer matrix forms.

Figure 2:
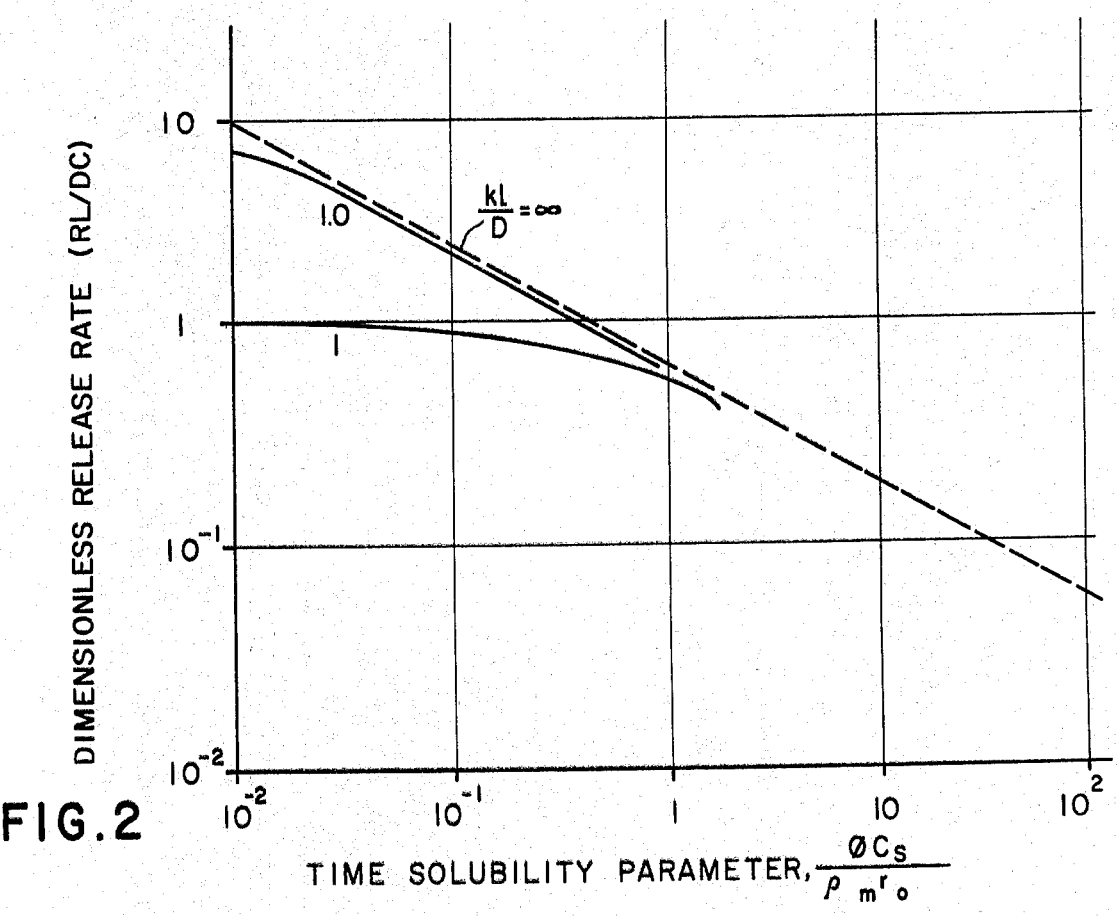

Another circumstance is that in which the matrix polymer and drug form no solid solution. This time parameter, in the case of implants which are wholly free from solid-solution relationships, can be expressed as $$\frac{\phi C}{\rho r}$$

wherein
$\phi = D\theta/L^2$
C = solubility of the active agent in an aqueous solution
$\rho$ = density of implant matrix
$r$ = weight fraction of chemical agent in the implant.
FIG. 2 illustrates such release rates.

The utilization of charts with the dimensionless time $\phi c/\rho r$ is in every way similar to that outlined above and optimum combinations of implant dimension, implant location, number of implanted particles, and duration of delivery may be selected for a desired dose rate.

Our understanding of drug release has therefore led to the discovery that when the drug and polymer matrix material form a solid solution the delivery of drug falls with time but the duration of drug delivery is independent of the initial loading of drug in the matrix. When solid solution is formed by the polymer matrix and the drug, the percent of the drug originally present released per unit time from a given implant thickness and surface area is dependent only on initial loading of the drug in the matrix.

Calculation of the release rates show that drugs which are dispersed within the polymer matrix without forming a solid solution are delivered at a more constant rate than drug/matrix combinations which form a single phase of solid solution. When the most regular release rate of drug is desired over the implant lifetime it is advantageous to utilize a bio-compatible polymer matrix material which does not form a solid solution with the drug of interest. In either case, the polymer matrix is selected so that it will degrade and be absorbed by the system being treated only after the treatment period.

In order to fully exploit the information developed above, it will be necessary, in some cases, to prepare a solid solution from a chemical/polymer system that normally would take the form of a matrix comprising a substantial quantity of undissolved, i.e. non-solute, chemical agent. For example, this might be done to extend the sustained release period. This may be accomplished by selecting a phase region in which both chemical and polymer are mutually soluble (e.g. by using a high temperature to melt the mixture alone or in combination with a solvent), then supercooling the mixture by quenching it to prevent crystallization of the separate phases. The preparation of the normal macroscopic dispersion form of a chemical (d-Norgestrel) in poly-DL-lactic acid is described in an Instructive Procedure set out below. The preparation of a solid solution of these two same components is described in Example 1.

In other cases, it may be desired to prepare a macroscopic dispersion from a system which ordinarily forms a solid solution.

Illustrative Example of the Invention

In order to point out more fully the nature of the present invention, the following working example is given as an illustrative embodiment of the present process and products produced thereby.

Instructive Procedure

This procedure is set forth to illustrate the matrix polymer preparation procedures, the test procedures for rate-of-release data and other such laboratory procedures which will serve as a background for understanding the illustrative examples of the invention. The Instructive Procedure discloses a material formed of a polymer matrix and active agent (a steroid) which do not in the normal course of events, form solid solutions and are not made to do so by this procedure. Consequently, the Instructive Procedure is not illustrative of the invention per se (except insofar as the release ratio will be indicative of some of the relationships on which the invention defined in the appended claims are based), but is descriptive of some techniques used in carrying out the subsequent examples.

In the synthesis of lactide (cyclic dimer of lactic acid), 2 liters of a 30 percent L(+) lactic acid solution containing 2 microcuries of tritiated sodium lactate was distilled at atmospheric pressure and then at 25 torr. After the water had distilled off, the pressure was decreased to 1 torr and the lactide was distilled while gradually raising the temperature to 225°. The crude product was then recrystallized twice with ethyl acetate, using 5ml for each 20g of lactide, and twice more from benzene; 120g of lactide (mp94–98°) were obtained.

For the conversion of this lactide to polylactic acid 137g of L (+) lactide was mixed with 0.85g tetraphenyl tin and heated for 6 hours in vacuo (0.05 torr) at 170° with intermittent stirring. The reaction produce was dissolved in dioxane and precipitated by dropwise addition to water. Drying of the precipitate at room temperature gave 120g of product. Estimates of molecular weight from gel permeation chromatography were a weight average of 70,400 and a number average of 27,400.

Films for the in vivo study were prepared from a suspension obtained by dissolving 3.5g polylactic acid in 26.5ml of boiling benzene, adding 4.5ml methanol, cooling to room temperature and adding 1.77g of 14C-labelled d-norgestrel (46.7uc/g), a product of Wyeth Laboratories, Radnor, Pennsylvania. The suspension was ball-milled to separate and subdivide the norgestrel. This dispersion was spread on a silicone treated plate using a Boston Bradley Adjustable Blade set at 25 mils. After air-drying, the films were evacuated overnight at 0.25 torr and had a final thickness of about 2.5 mils.

Four polylactic acid - $^{14}$C norgestrel films were implanted subdermally in each of four rats. Each strip averaged 0.9 × 2.5 × 0.0065cm size. The total surface area of film in each rat was 18.4 to 18.9 cm² and the total load, 13mg of norgestrel and 26mg of polylactic acid. Two of the strips were placed on either side of the posterior abdomen and two in the anterior lumbar vertebrae region. For the first 30 days, urine and feces were analyzed daily for radioactivity to follow the release of $^{14}$C-norgestrel from the implants. Subsequently, samples were collected every 48 hours for assay. Urine was analyzed by mixing 4ml with 16ml of a Triton X-100-toluene scintillation solution (1:2) containing 10g of 2,5-diphenyloxazole and 130 mg of 1,4-bis-2-(5-phenyloxazolyl)-benzene per liter. Quadruplicate samples were counted, two with and two without $^{14}$C internal standard. Feces were dried in vacuo and ground to a fine powder. Aliquots of 100–125mg size were combusted and analyzed for $^{14}$C.

Two rats were sacrificed after 87 days and two after 65 days. The implant residues were recovered and shaken in 3.0 ml 1M NaOH for 36 hours to hydrolyze the polylactic acid. The suspension was extracted and norgestrel recovered and determined.

The solution was extracted three times with two volumes of benzene:ethyl acetate (2:1) to isolate the norgestrel, which was assayed by gas chromatography on a 3 ft., 3% SE-30 column at 220°. The injector and flame ionization detector were set at 250° and nitrogen carrier flow was 60ml per minute.

Sodium lactate remained in the aqueous solution and was determined by converting it to acetaldehyde which was colorimetrically determined with p-phenylphenol. Calculation of the weight of polylactic acid remaining took into account the increase in weight by insertion of the elements of water incidental to hydrolysis.

Norgestrel release from the implants appearing in the urine and feces was initially about 5 micrograms per day per cm² of surface area. After 3 months the rate had declined to about 3 micrograms. The total material balance includes the steroid excreted in urine and feces and also the steroid and polylactic acid recovered in the implant is shown in Table I. The degree of variation between rats is indicated.

Table I. Recovery of $^{14}$C label in feces, urine, and residual implants and of polylactic acid in the residual implants after placing $^{14}$C-d-norgestrel polylactic acid films subcutaneously in rats.

TABLE I

| Rat No. | No. Days | Norgestrel Recovery | | | Polyactate Recovery |
|---|---|---|---|---|---|
| | | % In Feces | % In Urine | % In Residual Implant | % In Residual Implant |
| 1 | 87 | 36 | 14 | 28 | 69 |
| 2 | 87 | 29 | 8 | 33 | 82 |
| 3 | 65 | 34 | 12 | 25 | 81 |
| 4 | 65 | 22 | 9 | 41 | 88 |

When the polylactic acid films were recovered at autopsy, they were no longer rectangular in shape, but had shrunken to irregular shapes with significantly less surface area than the initial films.

The release performance observed in these experiments is consistent with drug release from a composition which did not form a solid solution and implantation at a site where a relatively high coefficient of mass transfer is attained in the tissue fluids surrounding the platelet-shaped drug sources.

EXAMPLE 1

This is an example of the formation of a solid solution and, in particular, an example of making a solid solution from a matrix/chemical agent system which (e.g. the instructive example) would not form such a solution under normal conditions.

One gram of poly-DL-lactic acid (PLA) and a quantity of 0.2 gms of d-Norgestrel powder were placed in a 250-ml vacuum flask. The flask was maintained for 15 minutes under a vacuum of 0.1 torr to remove water vapor. The flask was then heated in an oil bath at 175°C. for about 5 minutes in which time the PLA melted. The d-Norgestrel thereupon dissolved in the melted polymer. Then the flask was removed from the oil bath and immediately placed in a chamber maintained at 40°F.

After the contents of the flask had cooled to room temperature, they were in the form of a transparent solid and formed a stable solid solution, presumably a super-cooled solution.

The material has a release rate, when placed in a physiological environment, which is generally characterized by the curves of FIG. 1.

EXAMPLE 2

This Example illustrates the preparation of a solid solution in a system wherein said solution is easily achieved:

One gram of PLA and 0.5 grams of 2,4-dichlorophenoxy acetic acid (a herbicide sold under the generic trade designation 2,4-D) were dissolved in 10 ml of acetone. A clear, rather viscous solution was obtained. This solution was cast on a glass molding plate; the solvent flashed off. The remaining film was transparent and a stable solid solution.

This Example is to illustrate how an active agent and matrix combination which usually does form a solid solution can be prevented from doing so when the dosage rate is best achieved by the attainment of release rates characteristic of a system that is substantially free from contamination by a solid solution:

Two grams of PLA are dissolved in 20 ml of a solvent formed of equal volumes of acetone and benzene. The solution is spray-dried to form particles of about 100 microns in diameter. This material is maintained at 0.1 torr for 24 hours at 30°C. to remove residual solvent. The resultant material is a fluffy white powder.

A gram of the fluffy polymer powder is dry-blended with 0.5 grams of 2,4-D. The blending is achieved by processing in a 2-ounce jar mill for 24 hours using six ⅜-inch porcelain balls.

The mixture of polymer and chemical is then placed in a small conventional vacuum mold consisting of a chamber in which one gram of the mixture is charged. A vacuum of 0.1 torr is drawn to remove any air bubbles from the matrix. The temperature of the mold is raised to 100°C - then the approximate softening temperature of the polymer. The small brass plunger is then admitted into the mold chamber and the powdered mixture compressed to 7000 psi for 30 seconds. The mold is cooled and the pellet withdrawn.

The resulting material is not a solid solution.

It is also to be understood that the following claims are intended to cover all of the generic and specific features of the invention herein described and all statements of the scope of the invention which might be said to fall therebetween.

What is claimed is:

1. Solid-shaped articles for use as an implant in living tissue which implant is a means for administering at a more favorable dosage rate, said articles formed of (1) an active pharmaceutical chemical agent and (2) an organic polymer matrix, said agent and polymer normally forming a composition wherein there is substantial insolubility of one in the other, wherein said articles are formed of a composition of said agent and said polymer which is a solid solution and comprises substantially all of said agent in solution.

2. Articles as defined in claim 1 wherein said active agent is an organic pharmaceutical chemical.

3. Articles as defined in claim 2 wherein said organic chemical is a steroid.

4. Articles as defined in claim 2 wherein said organic polymer matrix is a poly(glycolic acid) or a polylactic acid.

5. Articles as defined in claim 1 wherein said solid solution is a supercooled solution containing a quantity of a solute that have substantial insolubility with said matrix when said matrix is in the liquid state.

6. Articles as defined in claim 1 wherein said active agent is an organic pharmaceutical chemical.

7. Articles as defined in claim 6 wherein said organic chemical is a steroid.

8. Articles as defined in claim 6 wherein said organic polymer matrix is a poly(glycolic acid) a polylactic acid.

9. Solid-shaped articles for use as an implant in living tissue which implant is a means for administering at a more favorable dosage rate, said articles formed of (1) an active pharmaceutical chemical agent and (2) an organic polymer matrix, said agent and polymer normally forming a composition wherein there is substantial solubility of one in the other, wherein said articles are formed of a composition of said agent and said polymer which there is no substantial solution of one in the other.

10. Articles as defined in claim 9 wherein said active agent is an organic pharmaceutical chemical.

11. Articles as defined in claim 10 wherein said organic chemical is a steroid.

12. Articles as defined in claim 10 wherein said organic polymer matrix is a poly(glycolic acid) a polylactic acid.

13. In a process for administering medication at more favorable dosage rates over an extended period of time by implanting into a host body a solid medicine-bearing implant formed of a polymeric matrix and an active medicinal agent which normally has substantial insolubility in said matrix, the improvement comprising the step of modifying the administering rate by implanting said matrix and agent in a composition which is a substantially complete solid solution of said matrix and said agent.

14. In a process as defined in claim 13 wherein said active agent is an organic pharmaceutical chemical.

15. In a process as defined in claim 14 wherein said organic chemical is a steroid.

16. In a process as defined in claim 14 wherein said organic polymer matrix is a poly(glycolic acid) or a polylactic acid.

17. A process for making a medicinal implant article for use as an implant in living tissue which implant is a means for administering at a more favorable dosage rate, said article being made from (1) a polymer matrix which is decomposable in a physiological environment into physiologically-tolerable decomposition products and (2) an organic pharmaceutical chemical which normally has substantial insolubility in said matrix polymer when said polymer is a solid state, said process comprising the mixing of said matrix and said polymer to form a solid solution which is stable under physiological conditions and free from said chemical in nonsolute form.

18. A process as defined in claim 17 wherein said article is formed by making a supercooled solution of said solute in said matrix.

19. A process as defined in claim 17 wherein said pharmaceutical is a steroid.

20. A process as defined in claim 19 wherein said polymer is a poly(lactic acid) or a poly(glycolic acid).

21. A process for making a medicinal implant article for use as an implant in living tissue which implant is a means for administering at a more favorable dosage rate, said article being made from (1) a polymer matrix which is decomposable in a physiological environment into physiologically-tolerable decomposition products and (2) an organic pharmaceutical chemical which is normally soluble in said matrix polymer when said polymer is in a liquid state, said process comprising the mixing of said matrix and said polymer without liquifying and matrix and thereby maintaining said pharmaceutical entirely in a non-solute state.

22. In a process for administering medication at more favorable dosage rates over an extended period of time by implanting into a host body a solid medicine-bearing implant formed of a polymeric matrix and an active medicinal agent which normally has substantial solubility in said matrix, the improvement comprising the step of modifying the administering rate by implanting said matrix and agent as a composition substantially free from any solution of said agent in said matrix.

* * * * *

UNITED STATES PATENT OFFICE
CERTIFICATE OF CORRECTION

Patent No. 3,976,071    Dated August 24, 1976

Inventor(s) Shafik E. Sadek

It is certified that error appears in the above-identified patent and that said Letters Patent are hereby corrected as shown below:

Change inventor's name to read S̲hafik E. Sadek

Column 5, line 33: change "14C" to read $^{14}C$

Claim 6, line 1 (Col. 7, line 67): change "1" to --5--.

Signed and Sealed this

Fifteenth Day of February 1977

[SEAL]

*Attest:*

RUTH C. MASON
*Attesting Officer*

C. MARSHALL DANN
*Commissioner of Patents and Trademarks*